United States Patent
Li et al.

(10) Patent No.: US 6,187,567 B1
(45) Date of Patent: Feb. 13, 2001

(54) METHODS AND REAGENTS FOR IN SITU AMPLIFICATION

(75) Inventors: Yuexia Li, Burtonsville; Kathy Lynn Hickman, Germantown; Eun Mi Lee, Gaithersburg, all of MD (US); Gregory John Hurteau, Clifton Park, NY (US)

(73) Assignee: Akzo Nobel N.V., Arnhem (NL)

( * ) Notice: Under 35 U.S.C. 154(b), the term of this patent shall be extended for 0 days.

(21) Appl. No.: 09/387,455

(22) Filed: Sep. 1, 1999

(51) Int. Cl.[7] .................................................. C12P 19/34
(52) U.S. Cl. .................................. 435/91.2; 435/6; 435/5
(58) Field of Search .................. 435/91.2, 6, 5

(56) References Cited

U.S. PATENT DOCUMENTS

| | | | |
|---|---|---|---|
| 4,886,741 | 12/1989 | Schwartz | 435/5 |
| 5,021,335 | 6/1991 | Tecott et al. | 435/6 |
| 5,168,038 | 12/1992 | Tecott et al. | 435/6 |
| 5,225,326 | 7/1993 | Bresser et al. | 435/5 |
| 5,506,105 | 4/1996 | Haydock | 435/6 |
| 5,521,061 | 5/1996 | Bresser et al. | 435/5 |
| 5,538,871 | 7/1996 | Nuovo et al. | 435/91.2 |
| 5,589,333 | 12/1996 | Bagasra et al. | 435/6 |

OTHER PUBLICATIONS

Teo et al., "PCR in situ: Aspects Which Reduce Amplification and Generate False–Positive Results," Histochemical Journal, vol. 27 (1995), pp. 660–669.

Fahy et al. PCR Methods and Applications 1:25–33. 1991.*

Haase et al. PNAS USA. vol. 87, p. 4971–4975, 1990.*

Teo, I.A., et al. "Polymerase chain reaction in situ; an appraisal of an emerging technique" Histochem J 27 (1995) No. 9, 647–659.

Zehbe, Ingeborg, et al., "In Situ PCR and Enzyme–Driven In Situ Amplification (In Situ 3SR) for the Detection of Viral DNA and mRNA", 240 Cell Vision, vol. 2, No. 3, 1995.

Zehbe, Ingebord, et al., "Self–Sustained Sequence Replication–Based Amplification (3SR) for the In Situ Detection of mRNA in Cultured Cells" 20 Cell Vision, vol. 1, No. 1 (1994).

Nuovo, Gerard, J., et al., "Importance of Different Variables for Enhancing In Situ Detection of PCR Amplified DNA" PCR Methods and Applications 2:305–312 (1993).

* cited by examiner

Primary Examiner—Jeffrey Fredman
Assistant Examiner—Juliet C. Einsmann
(74) Attorney, Agent, or Firm—Michael G. Sullivan (57) ABSTRACT

The present invention provides in situ amplification methods for the detection of a target nucleic acid molecule. The methods use a molecule termed "molecular tape" to retain the amplified target nucleic acid molecule within a cell upon amplification. The molecular tape, which may be used with a variety of amplification methods, improves the in situ detection of an amplified target molecule.

29 Claims, 3 Drawing Sheets

SEQUENCE LISTING

```
<160> NUMBER OF SEQ ID NOS:  5

<210> SEQ ID NO 1
<211> LENGTH: 25
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 1
aattctaata cgactcacta taggg                                         25

<210> SEQ ID NO 2
<211> LENGTH: 39
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 2
gaatgggata gagtgcatcc agtgtctcag tggggggac                          39

<210> SEQ ID NO 3
<211> LENGTH: 49
<212> TYPE: DNA
<213> ORGANISM: Simian-Human immunodeficiency virus

<400> SEQUENCE: 3
aattctaata cgactcacta tagggcacca gatgacgcag acagtatta               49

<210> SEQ ID NO 4
<211> LENGTH: 25
<212> TYPE: DNA
```

-continued

<213> ORGANISM: Simian-Human immunodeficiency virus

<400> SEQUENCE: 4
ctccgtcttg tcagggaaga aagca                                      25

<210> SEQ ID NO 5
<211> LENGTH: 44
<212> TYPE: DNA
<213> ORGANISM: Artificial Sequence
<220> FEATURE:
<223> OTHER INFORMATION: Description of Artificial
      Sequence:oligonucleotide

<400> SEQUENCE: 5
ttagctccat tagtgccaac aggctcagct ccgtcttgtc aggg                 44

METHODS AND REAGENTS FOR IN SITU AMPLIFICATION

FIELD OF THE INVENTION

The present invention relates to amplification and detection of target nucleic acid molecules. More particularly, the present invention relates to methods and reagents for retaining amplified target nucleic acid molecules within a cell upon amplification in situ, as well as for detecting the amplified molecules. The present invention thus improves the amplification and detection of a target nucleic acid molecule in situ.

In situ amplification and detection of nucleic acid molecules is useful for diagnosis, prognosis, drug efficacy determination, tissue pathology evaluation, patient monitoring, and many other clinical and research applications.

BACKGROUND OF THE INVENTION

Methods have been developed to study various aspects of gene expression to answer questions relating to, for example, how cells fulfill their various functions, how pathogens affect host cells, and how cells are transformed to a malignant state. In one method, RNA molecules may be isolated, amplified in a liquid phase, and then detected. However, this method does not reveal which cells are producing the RNA molecule of interest. In some instances, it is important to know what percentage of a cell population, or subset of a cell population, is expressing particular RNA molecules.

For instance, in most herpes virus infections, clinical disease corresponds with the production of certain viral RNAs in active infections, while not corresponding with the production of other viral RNAs or viral DNA that is produced during latent infection. As another example, HHV-8, which is thought to be the causative agent of Kaposi's sarcoma, has been found in Kaposi's sarcoma biopsies and peripheral blood samples. In situ studies indicate that viral infection is targeted to the endothelial (spindle) cell component thought to be the central cell in the pathogenesis of the lesion. Certain transcripts are thought to be indicative of viral replication, and detection of these transcripts may be able to distinguish latent from active infections (Zhong et al. (PNAS 93:6641(1996)).

In situ amplification may also be used for detecting human papilloma virus (HPV) infections and for determining the role the virus plays during transformation of cervical cells (See U.S. Pat. No. 5,506,105). Certain HPV transcripts are produced only in cells actually transformed to the malignant state, and the detection of these transcripts therefore corresponds specifically with the detection of early malignancy.

Nucleic acid amplification has also been used advantageously for detecting HIV-1 exposure in seronegative sexual partners of HIV-1 seropositive individuals, in HIV-1 seronegative infants and children, and in health care workers accidentally exposed to HIV-1 positive blood or body fluids. The ability to identify individual cells, either latently or productively infected, under the microscope would be very useful for delineating a latent state and emergence from it. This would be useful not only for understanding the development of infection, but also as a more direct quantitative measure of the effect of antiviral therapy. Further, the ability to identify individual infected cells would help understand the mechanism of HIV-1 transmission.

Thus, there exists a substantial interest in detecting in cells and tissues the distribution and/or expression of RNA molecules. In situ amplification of RNA targets, for example, provides a powerful technique to differentiate neighboring cells in a histochemical or cytochemical preparation with respect to somatic mutation, pathogenic infection, oncogenic transformation, immune competence and specificity, state of differentiation, developmental origin, genetic mosaicism, cytokine expression, and other characteristics useful for understanding both normal and pathological conditions in eukaryotic organisms.

In some instances, levels of target nucleic acids are sufficiently high such that they can be visualized with in situ hybridization using a labeled probe. However, at least one limitation inherent in such techniques is the copy number of the target molecule; the detection of RNA molecules by hybridization typically requires tens to hundreds of copies of the target nucleic acid molecule per cell. In many instances, the target nucleic acid molecules of interest are present only at low levels, in which case other techniques must be used.

PCR has been employed to amplify low copy number nucleic acids so that sufficient amounts of target sequence are available for hybridization and subsequent visualization (Haase et al., PNAS 87:4971, 1990). While this technique overcomes the problem of low copy number, methods involving thermal cycling may have a deleterious effect on the structure of cells and tissues. For instance, it may be difficult after thermal cycling to identify or classify the cells that contain the desired transcript, thus reducing the advantages and useful information gained from using the PCR method.

The sensitivity of PCR amplification has been combined with the target localization of in situ hybridization to create in situ PCR, wherein PCR is performed within chemically fixed cells (Haase et al 1990, PNAS 87:4971). Haase et al. used a series of overlapping primer pairs specific to overlapping target sequences within the genome of selected organisms to improve the retention of amplified target nucleic acids within cellular compartments.

One variation of conventional PCR is RT/PCR, which detects target RNA sequences in test samples via complementary DNA (cDNA) sequences reverse transcribed from the target RNA; the cDNA is then detected using conventional PCR (Kawasaki et al., 1988, PNAS 85(15):5698, and Rappolee et al., 1989, J. Cell. Biochem. 39:1–11). However, prior methods utilizing RT/PCR also have certain limitations, including, in addition to its deleterious effect on morphology, RT/PCR requires that only RNA be amplified in a background of DNA. In vitro RT/PCR methods solve this problem in two general ways: 1) DNase treatment, and 2) differentiation of the RNA amplification product from the DNA amplification product. Option 1 is more difficult to perform in in situ preparations than in reactions in solution. Option 2 usually requires that the two possible amplification products have different sizes and be resolved differently on a gel. Option 2 also requires that the two possible products hybridize to different sequences and differently labeled probes, thus also limiting this option in in situ methods.

In situ amplification methods also suffer from the problem that the amplification products, being small molecules, may diffuse from the cell as a result of permeations made in the cell surface to allow amplification reagents to enter the cell. There thus exists a need to prevent this phenomenon, called leakage, from occurring. In situ amplification methods thus demand a balance between, first, permeabilizing sufficiently the cell membrane to allow the amplification reagents to reach the target nucleic acid, and second, maintaining sufficient integrity in the membrane to prevent leakage of the amplifed target material and enable detection.

Methods for solving the leakage problem during in situ PCR amplification have used multiple primer sets. Such methods produce overlapping amplification products of different sizes, wherein the products are partially double-stranded, each strand having overhanging ends that can hybridize to one another to form large concatamers and retard diffusion from the cell. However, in addition to suffering from the above drawbacks associated with standard in situ PCR (e.g., poor morphology due to the thermal cycling), the use of multiple primer pairs to solve the leakage problem has additional disadvantages, including the increased expense for their production and the inherent problem that with many target organisms, such as pathogenic viruses, it is hard to find even a few short sequences that will make good primer and probe sites. The use of multiple primer pairs also has the disadvantage of increasing the likelihood of non-specific background amplification. Furthermore, other important abnormal target sequences such as activated oncogenes, inactivated tumor suppressor genes, and oncogenic chromosomal translocations involve somatic point mutations and chromosomal rearrangements that are distinguishable from the parental (normal) sequence only when amplified from single primer pairs.

Thus, there exists a need for improved ways to retain amplified target nucleic acid molecules within a cell, and thereby improve amplification and detection results.

Thus, one object of the invention is to provide ways for improving the detection of a target nucleic acid molecule after amplification in situ.

Another object of the invention is to provide ways to retain an amplified target nucleic acid molecule within a cell upon amplification in situ.

Yet another object of the invention is to provide an efficient way for detecting a target nucleic acid molecule once amplified in situ.

Still another object of the invention is to provide ways for maintaining the proper morphology of cells and tissue sections.

SUMMARY OF THE INVENTION

The present invention relates to methods and reagents for in situ amplification of target nucleic acid molecules. The present invention solves a problem associated with in situ amplification, referred to as leakage, which results from permeabilizing cell membranes to permit amplification reagents to enter the cell.

The present invention thus provides a method for preventing an amplified target nucleic acid molecule from leaking from a cell. The method comprises the step of exposing the cell to a novel reagent termed "molecular tape" that enters the cell and hybridizes with the amplified target molecule to form a complex. By forming such a complex, the amplified target molecule, otherwise small enough to leak from the cell, can remain within the cell for detection in situ.

The present invention may be practiced with most, if not all, types of amplification reactions, including amplification involving thermal cycling, such as PCR and RT-PCR. A preferred embodiment of the present invention is practiced using isothermal amplification, including isothermal transcription-based amplification, such as nucleic acid sequence-based amplification (NASBA).

In some embodiments of the invention, the molecular tape, complexed with the amplified target molecule, may further bind to one or more intracellular constituents such as actin.

The target nucleic acid molecule may be any nucleic acid molecule, including DNA and RNA, and their analogs, and is preferably RNA.

In addition to cells, cultured or otherwise, the methods and reagents of the present invention may be used to amplify and detect target nucleic acid molecules in other samples, including tissue sections. Further, the cell within which a target nucleic acid molecule is amplified and detected in accordance with the invention may be one of a plurality of suspended cells.

The amplified target nucleic acid molecule may be detected in accordance with the present invention in situ, or alternatively, after cell lysis using various detection methods that can confirm the presence of the amplified target molecule. If detection occurs in situ, various detection methods and detectable labels also are useful. For example, the molecular tape itself may comprise a detectable label, preferably a fluorescenylated moiety.

The methods and reagents of the present invention offer the advantage that even the smallest amplifed target nucleic acid molecule may be retained within a permeabilized cell to permit its detection.

DETAILED DESCRIPTION OF THE INVENTION

As stated above, the present invention provides a method for preventing an amplifed target nucleic acid molecule from leaking from a cell upon amplification in situ. The "leakage" is prevented as the result of a reagent termed "molecular tape" that enters the cell and hybridizes with the amplified molecule to form a complex. The formation of the complex prevents leakage. In general, the molecular tape is capable of forming complexes with amplified target molecules wherever the amplifed target molecules may be found in an in situ reaction.

The term "leak" and other forms of this word (e.g., leakage, leaking) are defined as the undesired exiting from a cell of an amplified target nucleic acid molecule, which may occur during and after in situ amplification of the target molecule. Leakage may occur, for example, as a result of permeabilizing the cell membrane to allow amplification reactants to enter the cell to effect in situ amplification. The openings in the membrane left as a result of the permeabilization may enable amplification products small enough to pass through these openings to exit, and thus leak from, the cell.

The term "prevent" and other forms of the word are used broadly to include inhibiting, decreasing and/or stopping leakage.

The term "molecular tape" is defined to include various forms of nucleic acid molecules, including single-stranded as well as double-stranded molecules, which perform the function of retaining an amplified target nucleic acid molecule within a cell upon amplification in situ. The molecular tape can cause the amplified target nucleic acid molecule to remain within the cell by various mechanisms.

Figure 1:
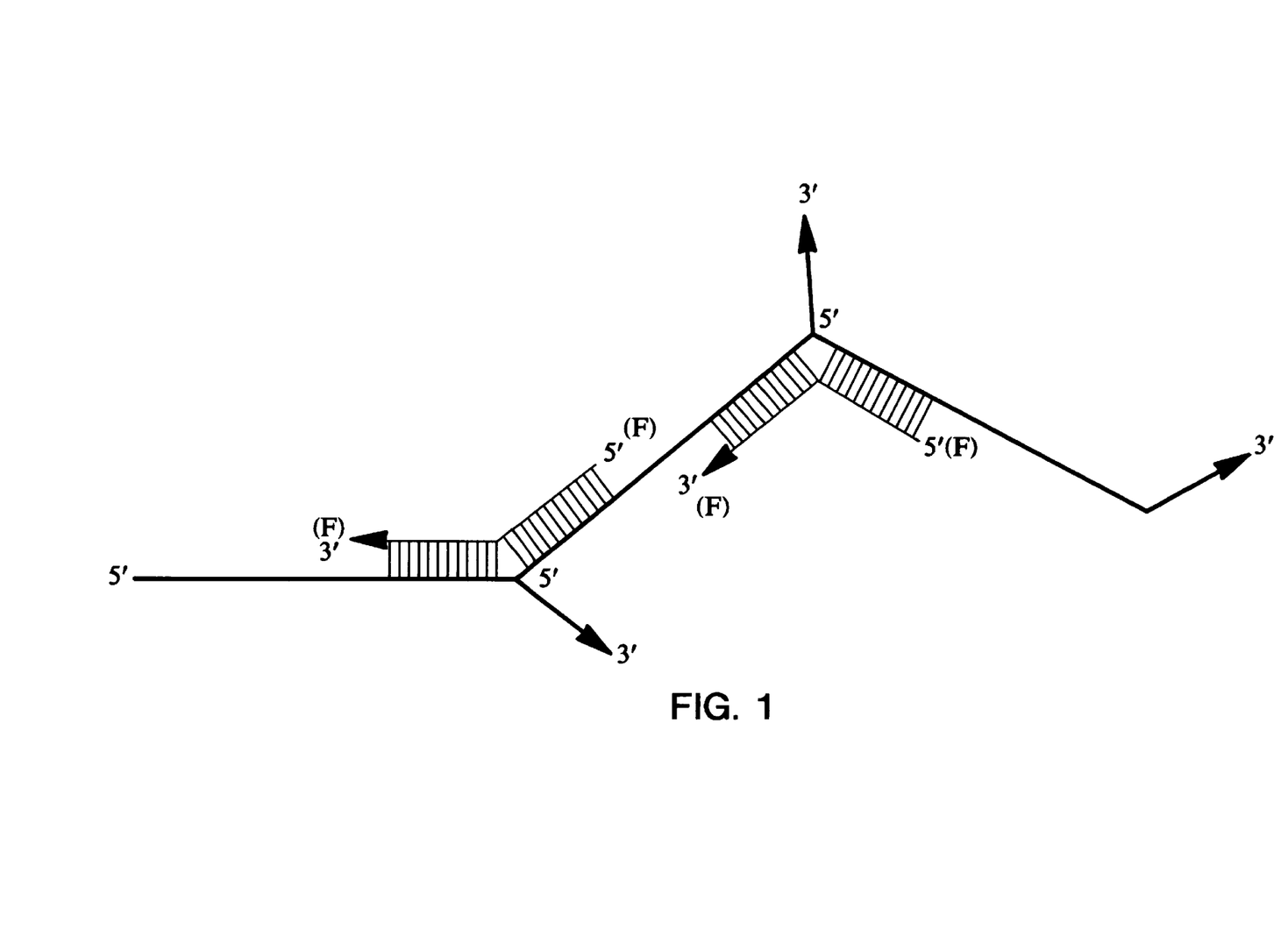
FIG. 1 depicts a complex of molecular tape and an amplified target molecule in accordance with a preferred embodiment of the invention.

In one embodiment of the invention, the molecular tape may hybridize with one or more copies of the target molecule upon amplification. Hybridization may occur, for example, between separate nucleic acid sequence regions on the molecular tape and complementary regions on the amplified target molecule. This embodiment thus may cause the formation of complexes or concatamers comprising one or more molecules of molecular tape, wherein a first sequence region of the molecular tape hybridizes with a complementary region of a first copy of the amplified target molecule (or amplicon), and a second sequence region of the tape hybridizes with a complementary region of a second copy of the amplifed molecule. The complexes or concatamers formed in accordance with the invention typically comprise a plurality of molecules of molecular tape hybridizing with complementary regions on one or more copies of the amplified target molecule, and thereby causing multiple copies of the amplified target molecule to be complexed together. For example, a preferred embodiment of the invention is depicted in FIG. 1, which shows a plurality of molecular tapes (grey) hybridizing with, first, a complementary region at the 5' end of the amplifed target molecule (black), and second, a complementary region upstream from the 3' end of the amplified target molecule. As stated above, the sizes of the complexes and concatamers formed in accordance with the invention should for the most part exceed the sizes of most, if not all, openings present in the cell membrane, for example, as a result of permeabilizing the membrane, as described above.

In another embodiment of the invention, the complex formed by the interaction of an amplified target molecule and the molecular tape may further interact with an intracellular constituent such as an organelle or a structural protein (e.g., actin) as an additional means for preventing leakage.

The molecular tape may have a variety of different lengths, with a longer lengthed molecular tape capable of causing the interaction between multiple copies of the amplified target molecule. The molecular tape should be long enough to form a complex of two or more copies of an amplified target molecule, or alternatively a complex of at least one copy of the amplified target molecule and an intracellular constituent. The length of the molecular tape may range from about 20 nucleotides to a nucleotide length compatible with the length of the target molecule, that is, a length preferably shorter than the nucleotide length of the target molecule and which does not interfere with amplification of the target molecule. In a preferred embodiment, the length of the molecular tape may range from about 20 to about 60 nucleotides, with a more preferred range of about 30 to about 50 nucleotides. Additional features and advantages of the molecular tape in accordance with the invention will be evident from the following description and examples.

Additionally, measures may be taken in accordance with the present invention, if necessary, to ensure that the molecular tape does not function as a primer. These measures may include, for example, blocking the 3' end of the molecular tape to prevent any priming reaction.

The molecular tape may comprise sequences of DNA or RNA, or analogs thereof, such as peptide-containing nucleic acids.

In one embodiment of the present invention, the molecular tape may comprise a detectable label, thus functioning both as molecular tape and a detection probe. FIG. 1 shows an example of a fluorescenylated molecular tape, wherein the fluorescein moiety is attached (e.g., covalently linked) to both the 5' and 3' ends of the tape.

Molecular tape in accordance with the invention may be produced using commercially available synthesis of oligonucleotides according to pre-determined specifications for the nucleotide sequence of the tape. These specifications may be determined by selecting, for example, two separate sequence regions in the target nucleic acid molecule and synthesizing an oligonucleotide containing separate regions complementary to the above regions. An example of this is shown in FIG. 1, which shows a preferred embodiment of the present invention. The molecular tape may then be tested experimentally in an amplification reaction, such as the preferred NASBA reaction, in which the ability of the molecular tape to prevent leakage of the amplified target molecule may be measured using detection methods described herein.

The term "nucleic acid" is defined to include DNA and RNA, and their analogs, and is preferably RNA. Further, the methods of the present invention are not limited to the detection of mRNAs. Other RNAs that may be of interest include tRNAs, rRNAs, and snRNAs.

The term "intracellular constituent" means any constituent within a cell that is capable of reacting, in some instances after modification, with the molecular tape and further cause the complex of molecular tape and the amplified target nucleic acid molecule to be retained within the cell. The intracellular constituent(s) thus may provide an additional means for preventing leakage. Intracellular constituents may include, for example, organelles and intracellular structural proteins such as actin.

The term "primer" as used herein refers to an oligonucleotide which is complementary to, and is capable of promoting the synthesis of, a nucleic acid sequence (as template or target sequence) under suitable conditions (e.g., buffer, salt, temperature and pH) in the presence of nucleotides and an agent for nucleic acid polymerization, such as DNA dependent or RNA dependent polymerase. A primer should be long enough to hybridize with an appropriate target area and be capable of promoting the synthesis of complementary nucleic acid sequences in the presence of polymerization agents. A typical primer contains a sequence length of at least 10 nucleotides and is substantially complementary or homologous to the target sequence. Primers preferably contain about 15–26 nucleotides, but longer primers also are useful, for example, in transcription based techniques such as NASBA in which one of the primers contains an additional promoter sequence encoding a polymerase promoter.

The term "promoter sequence" defines an oligonucleotide that is recognized by a polymerase, such as RNA polymerase. In principle, any promoter sequence may be employed for which there is a known and available polymerase that is capable of recognizing the initiation sequence. Known and useful promoters include those recognized by certain bacteriophage RNA polymerases such as bacteriophage T3, T7 or SP6. Further, the use of the promoter sequence as part of the primer, e.g., the starting point for an elongation reaction, may be blocked in certain embodiments of the invention. A particularly preferred promoter sequence is that encoding the T7 RNA polymerase promoter (AATTCTAATACGACTCACTATAGGG)(SEQ ID NO:1), which promoter is used in NASBA, a preferred isothermal transcription-based amplification system in accordance with the present invention.

A. Samples

As stated above, the methods and reagents of the invention may be used for in situ amplification and detection in various types of samples, including tissue sections and suspended cells.

Tissue and cell samples used in connection with the invention may be obtained from various different mammalian sources, including but not limited to human tissue and cell samples. Cell samples may be obtained from tissue aspirates and bodily fluids. The invention may be used with transformed or hyperplastic cells, or cells obtained from carcinomas. For example, human blood cells, particularly peripheral blood mononuclear cells (PBMCs), are often used for studying HIV-1 and HIV-2.

Tissue sections may be obtained in several different ways, including by cryostat sectioning or microtome slicing, or the like. Tissue may be obtained from any of a number of different sources, including solid organs such as brain, spleen, bone, heart, vascular tissue, lung, kidney, liver, pituitary or endocrine glands, lymph node, dispersed primary cells, tumor cells or others. Of particular importance for clinical samples are lymphoid tissue and suspected tumor tissues and cells.

Tissues may be pretreated in conventional ways prior to sectioning. A sectioned tissue sample may be fixed by conventional techniques, which do not interfere with subsequent processing. The particular manner in which a tissue sample is fixed is not critical, as long as the integrity of the target nucleic acid molecules is maintained, and the fixing procedure does not interfere with subsequent process steps.

Cell and tissue samples also may be obtained by standard techniques such as scraping, lavage, or biopsy. Primary cells or established cell lines may be grown in culture on a support or grown in suspension and centrifuged onto a support.

B. Pre-Amplification Processing

Cell and tissue samples may be fixed by any known conventional fixation technique. A preferred fixation technique for use with the present invention involves a combination of cross-linking and precipitive fixatives for cells, as well as cross-linking fixatives alone (such as 10% neutral buffered formalin) for tissue sectioning. Thus, the selected target nucleic acid molecule can be well preserved along with cell/tissue morphology.

Tissue and cell samples are prepared in conventional ways for microscopy, which may include dehydration and rehydration of the samples with known solvents, followed by washes with standard buffers, such as phosphate buffered saline (PBS).

Furthermore, since it is known that cells prepared for in situ amplification may be fragile, centrifuge times and speeds should be selected carefully to obtain good results.

For instance, the speeds and times indicated in the following examples, in which H9 cells are used, may require slight adjustment for different cell types.

Cell samples may be grown on appropriate supports, such as slides for light microscopy or grids for electron microscopy, or alternatively may be grown without the support and later applied to the support.

C. Amplification Methods

As stated above, amplification may be conducted under isothermal conditions.

In a preferred embodiment of the invention, an isothermal transcription-based amplification system may be performed based on the coordinated activities of three enzymes (reverse transcriptase, RNase H, and RNA polymerase) and two DNA oligonucleotides (referred to herein as primers) specific for the target sequence. The method starts with an RNA template and alternately synthesizes DNA and RNA. Specifically, starting with the desired RNA template, a primer, dNTPs, and reverse transcriptase, an RNA/DNA hybrid is generated. The RNA is degraded from the hybrid by RNase H activity. A double stranded DNA is then generated by the reverse transcriptase using the second primer, and then the double stranded DNA functions as template for synthesizing large amounts of RNA by using the RNA polymerase in the presence of NTPs. These synthesized RNA molecules can then serve as templates in subsequent amplification cycles. One of the primers has, in addition to the sequences complementary to the template, additional sequences necessary for generating a promoter and transcription initiation site. Preferred promoters and transcription initiation sites are those recognized by bacteriophage RNA polymerases, such as T3, SP6, and T7. The three enzymatic activities may be provided by three separate enzymes, reverse transcriptase, RNase H, and RNA polymerase, or by only two enzymes, reverse transcriptase and RNA polymerase, with the RNase activity supplied by the reverse transcriptase. Preferably the reverse transcriptase is avian myeloblastosis virus reverse transcriptase (AMV-RT) and the RNA polymerase is T7 RNA polymerase.

A preferred isothermal transcription based amplification system for use with the present invention is NASBA. The NASBA method is disclosed in U.S. Pat. Nos. 5,409,818 and 5,554,527, which are incorporated herein by reference. NASBA includes the use of T7 RNA polymerase to transcribe multiple copies of RNA from a template including a T7 promoter.

Another technique for the amplification of nucleic acids is the so-called transcription based amplification system (TAS). The TAS method is described in International Patent Application No. WO 88110315, which is herein incorporated by reference. Transcription based amplification techniques usually comprise treating target nucleic acids with a pair of oligonucleotides, one of which comprises a promoter sequence for generating a template which includes a functional promoter. Multiple copies of RNA can be transcribed from the template and can serve as a basis for further amplification.

Other transcription based amplification techniques are described in EP 408295, which is herein incorporated by reference. EP 408295 is primarily concerned with a two-enzyme transcription based amplification method.

As stated above, amplification may also be conducted using thermal cycling. A preferred technique is the polymerase chain reaction (PCR), which is described in U.S. Pat. Nos. 4,683,202 and 4,683,195, each incorporated herein by reference.

The PCR method also can be used to amplify a desired RNA target. This technique (known as RT-PCR) includes a preliminary step using reverse transcriptase (RT) to produce a single stranded DNA sequence complementary with the RNA target. This DNA sequence is then reacted with a second primer to produce a second DNA strand complementary with the first strand. This double stranded DNA can then be amplified using PCR.

D. Detection Methods

Many methods are known in the art for in situ detection of nucleic acids, any of which may be used with the methods of the present invention. Detection methods are typically one of two general types: 1) incorporation of a labeled nucleotide during the amplification reaction, and 2) hybridization with a labeled nucleic acid or analog that specifically hybridizes with a region of an amplification product.

In either general method, the label may be a radioactive isotope, an enzyme, or any other moiety capable of generating a detectable signal, including calorimetric, fluorescent, chemiluminescent and electron dense signals.

Autoradiography with $^3H$, $^{125}I$, $^{35}S$, $^{14}C$, or $^{32}P$ labeled probes can be used in which the isotope is part of the base or sugar moieties, or is attached to the nucleotide via some linking group. Other labels include ligands which are covalently bound to a probe. The ligand then binds to an anti-ligand, which is either inherently detectable, or covalently bound to a detectable signal system such as an enzyme, a fluorophore, or a chemiluminescent compound. Enzymes of interest include phosphatases, esterases or glycosidases, or oxidoreductases such as peroxidase. Fluorescent compounds include fluorescein and its derivatives, rhodamine and its derivatives, dansyl, umbelliferone, etc. Chemiluminescent compounds include luciferin and 2,3-dihydrophthalazinediones.

For example, detection may occur as a result of a biotin-avidin interaction, with the avidin being labeled with fluorophores, enzymes, or other labels. Fluorophores of interest may include phycobiliproteins, fluorescein, or the like. Enzymes may include horseradish peroxidase, phosphatase, or the like. Alternatively, labels such as colloidal gold or ferritin may be used for detection by electron microscopy.

Molecular beacons may also be used to detect amplification product (Tyagi and Kramer, Nature Biotech. 14:303, 1996). Molecular beacons are nucleic acid probes that recognize and signal the presence of target nucleic acids. Specifically, the beacon molecules are single stranded nucleic acids or nucleic acid analogs that possess a stem and loop structure. The loop portion of the molecules is a probe sequence that is complementary to the target sequence; the stem is formed by the annealing of two complementary arm sequences on either side of the probe sequence. A fluorescent moiety is attached to the end of one arm, and a fluorescent quenching moiety is attached to the end of the other arm. When the loop portion forms a hybrid with the target sequence, the fluorophore and quencher are separated, and the fluorophore fluoresces when illuminated by ultraviolet light. If the loop portion does not hybridize to a target sequence, the fluorophore and quencher remain in close proximity and the fluorophore does not fluoresce.

In a preferred embodiment of the invention, the amplified target molecule may be detected as a result of one or more detectable labels on the molecular tape. The detectable label may include the above types of labels.

The methods of the present invention also may be used in conjunction with immunological methods such as immunostaining or fluorescent activated cell sorting (FACS). Multiple staining of, for example, cell-surface antigens, permits disease diagnosis and prognosis based on infection rates of cellular subpopulations. In situ amplification in conjunction with other staining methods applied to blood or biopsy samples from patients believed to be infected with lymphotrophic retrovirus, such as HIV-1, should yield valuable prognosis information such as the fraction of CD4$^+$(surface antigen) cells expressing specific viral genes.

As stated above, the amplified target molecule may be detected after cell lysis using various detection methods to confirm the intracellular presence of the amplified target molecule. One method is electrochemiluminescence chemistry (ECL), which uses a biotinylated oligonucleotide capture probe immobilized on the surface of a streptavidin-coated magnetic bead via a biotin-avidin interaction. The system also uses an oligonucleotide detector probe, which is hybridizable with an independent region of the amplification product. The detector probe is labeled with Ruthenium, which can generate the ECL signal.

The present invention is described by reference to the following Examples, which are offered for illustration and are not intended to limit the invention in any manner.

EXAMPLE 1

Standard Isothermal Amplification Method I (Cells on Slides) Pre-amplification:

Cultured cells are collected and spun at 1400 rpm (377 g) for 10 minutes. Cells are washed with 1X PBS twice at 1200 rpm (270 g) for 8 minutes. The cells are resuspended in 1X PBS at a concentration of approximately $5-10 \times 10^6$/ml and fixed in 1 volume cells to 9 volume fixative (1:1 acetone:methanol) for 30 minutes. The cells are then washed with 1X PBS once and resuspended at a concentration of $2 \times 10^5$/ml in 1X PBS. The cells are spun onto silianated (Shandon Lipshaw) slides at 700 rpm for 5 minutes with a cell number of $5 \times 10^4$/slide (250 µl/slide of $2 \times 10^5$ cells/ml). The slides are then allowed to air dry for 3 hours to overnight at room temperature (R.T.) and washed 2 minutes with dd $H_2O$ at R.T., and again air-dried at least 30 minutes at R.T. NASBA Amplification:

Amplification is achieved in a 20 µL reaction containing a 15 µL solution comprising the following components: 40 mM Tris, pH8.5; 12 mM $MgCl_2$; 70 mM KCl; 5 mM DTT; 1 mM dNTPs (each); 2.0 mM each of rATP, rCTP, and rUTP (mixture of UTP and digoxigenin labeled UTP); 1.5 mM rGTP; 0.5 mM ITP; 15% DMSO; 0.2 µM of primer 1 and primer 2; 4 picomole molecular tape, 1.5 M sorbitol, and a 5 µL of enzyme mix including 2.1 µg BSA; 32 units of T7 RNA polymerase; and 25.6 units of AMV reverse transcriptase (AMV-RT). If digoxigenin-UTP is used, the concentration of the dig-UTP should be about 10–20% of the total concentration of UTP.

The procedure is carried out as follows:

1. Mix the first 15 µl reaction mix well and then add the second 5 µl enzyme mix and mix gently (without vortexing).
2. Add total 20 µl onto the reaction chamber (MJ Research) on the top of the slide and seal the chamber carefully.
3. Incubate the slides at 41° C. for 2 hours on a "Hybaid" slide incubator.

Post Amplification:

Wash the slide twice with 1 X PBS, twice with 0.5 X PBS, and twice with dd$H_2O$, for 5 minutes for each wash. Dehydrate with ethanol: 50%, 2 minutes; 70%, 2 minutes; 90%, 2 minutes; 95%, 2 minutes; and 100%, 2 minutes, and air dry for about 10 minutes. Samples are then serum blocked (using the same serum that anti-dig was derived from) with 5% serum, 1% fetal bovine serum, 5% BSA for 1 hour at R.T., and anti-dig antibody is applied overnight at 4° C. The samples are then washed twice with 1 X PBS, twice with dd$H_2O$. The substrate is then added if using an enzyme conjugated anti-dig antibody, or the cells are monitored immediately under a microscope if using FITC conjugated anti-dig antibody or fluorescein labeled molecular tape.

EXAMPLE 2

Standard Isothermal Amplification Method II (Cells in Suspension) Pre-amplification:

Cultured cells are collected and spun at 1400 rpm (377 g) for 10 minutes. The cells are washed with 1 X PBS twice at 1200 rpm (270 g) for 8 minutes. The cells are resuspended in 1 X PBS at a concentration of approximately $5-10 \times 10^6$/ ml and fixed in 1 volume cells to 9 volume fixative (1:1 acetone:methanol) for 30 minutes. The cells are then washed twice with 1 X PBS at 53 g for 15 minutes. The cells are then subjected to pronase digestion for 5 minutes at 37° C. Digestion is then followed by heat inactivation for 10 minutes at 90° C. The cells are then again washed twice with 1 X PBS at 53 g for 15 minutes. After the last wash, the cells will remain in a volume of 1 X PBS not to exceed 30 µl if the starting cell number was 2.5–5.0×10⁶ cells.

NASBA Amplification:

Amplification is achieved in a 20 µL reaction containing 1) a 10 µL solution comprising the following components: 40 mM Tris, pH8.5; 12 mM MgCl₂; 70 mM KCl; 5 mM DTT; 1 mM dNTPs (each); 2.0 mM each of rATP, rCTP, and rUTP (mixture of UTP and digoxigenin labeled UTP); 1.5 mM rGTP; 0.5 mM ITP; 15% DMSO; 0.2 µM of primer 1 and primer 2; 4 picomole molecular tape, 1.5 M sorbitol, 2) a 5 µL of enzyme mix including 2.1 µg BSA; 32 units of T7 RNA polymerase; and 25.6 units of AMV reverse transcriptase (AMV-RT). (If digoxigenin-UTP is used, the concentration of the dig-UTP should be about 10–20% of the total concentration of UTP.), and 3) 5 µl of cells in 1 X PBS from the above pre-amplification step.

The procedure is carried out as follows:
1. Mix the first 10 µl reaction mix well and then add the second 5 µl enzyme mix and mix gently (without vortexing).
2. Add the above 15 µl (components 1 and 2 above) to 5 µl cells in an eppendorf tube. Mix gently the total 20 µl in the tube.
3. Incubate the tubes at 41° C. for 2 hours.

Post-amplification:

The cells are washed twice with 1 X PBS at 53 g for 15 minutes. The samples are then serum blocked (using the same serum that anti-dig was derived from) with 5% serum, 1% fetal bovine serum, 5% BSA for 1 hour at R.T., and anti-dig antibody is applied overnight at 4° C. The samples are then washed twice with 1 X PBS. The substrate is then added if an enzyme conjugated anti-dig antibody was used, or the cells are ready for analysis by an FACS machine if FITC conjugated anti-dig antibody or molecular tape was used. If a commercially available fluorescence system is used in combination with enzyme conjugated anti-dig antibody, the manufacturer recommended procedure is followed after overnight antibody incubation.

EXAMPLE 3

Standard Isothermal Amplification Method III (Tissue Sections)

Pre-Amplification:

A standard fixed tissue section is de-paraffinized with xylene twice, 5 minutes each time, followed by washing in 100% ethanol twice, 5 minutes each time. The section is then rehydrated with 95%, 90%, 70%, and 50% ethanol, 2 minutes for each treatment, followed by 2 minutes with ddH₂O. The section is then subjected to protease digestion by one of two methods (A) Dispase II and pronase mixture for 30 minutes at 37° C., or B) protease K for 30 minutes at 37° C. For both methods, enzymes must be inactivated at 90° .C for 10 minutes after the 37° C. After protease digestion, the section is washed twice with 1 X PBS, 2 minutes for each wash, followed by washing twice with ddH₂O, 2 minutes for each wash. The section is then dehydrated with 50%, 70%, 90%, 95%, and 100% ethanol, 2 minutes for each treatment, followed by air drying for about 10 minutes.

NASBA Amplification:
  Same as Example I.
Post Amplification:
  Same as Example I.

EXAMPLE 4

The effectiveness of the molecular tape of the present invention for retaining amplified target nucleic acid molecules within a cell was tested.

Two cultures of H9 (immortalized human T cell line) cells were cultured (in RPMI with 10% fetal calf serum) and trypan blue stained for counting. One culture was infected with HIV-1 IIIB, while the other culture was not. Cells were allocated as follows: Group I contained 0% infected cells; Group II contained 50% infected cells; and Group III contained 100% infected cells. See FIG. 2.

Samples of each group of cells were prepared for amplification and amplified according to the procedures in Example 1 above, which included the incorporation of digoxigenin-UTP, as described. The NASBA primers used are included in a NASBA-based HIV amplification and detection kit ("Nuclisens HIV-QT"), available from Organon Teknika, Durham N.C. Half of the cells of each group were lysed after dehydration, while the other half were treated according to the above in situ procedures. All groups were then subjected to detection, using either FITC conjugated anti-dig antibody for in situ detection or ECL detector and capture probes for the lysed cells.

As shown in Table 1, for the cells lysed after dehydration, it was found using ECL detection that while no detectable amplified target molecule remained within cells in the absence of molecular tape (MT), as denoted by "negative", the amplified target molecule was detectable inside cells when using molecular tape, as denoted by "positive". The molecular tape contained the sequence: GMTGGGATAGAGTGCATCCAGTGTCTCAGTGGGG-GGAC(SEQ ID NO:2). The "negative" and "positive" designations corresponding to the ECL signals inside cells (with or without molecular tape) were determined based on the ECL numbers obtained experimentally for Groups I–III. Specifically, when the ECL number is less than 2.5 times the value of a pre-determined ECL assay negative (calculated based on a standard algorithm used in the ECL system, which is also part of the "Nuclisens HIV-QT" kit, including detection and capture probes, from Organon Teknika), the ECL signal is considered negative.

TABLE 1

|  | ECL signals inside of cells (without MT) | ECL signals inside of cells (with MT) |
| --- | --- | --- |
| Experiment 1 | Negative | Positive |
| Experiment 2 | Negative | Positive |

Figure 2:
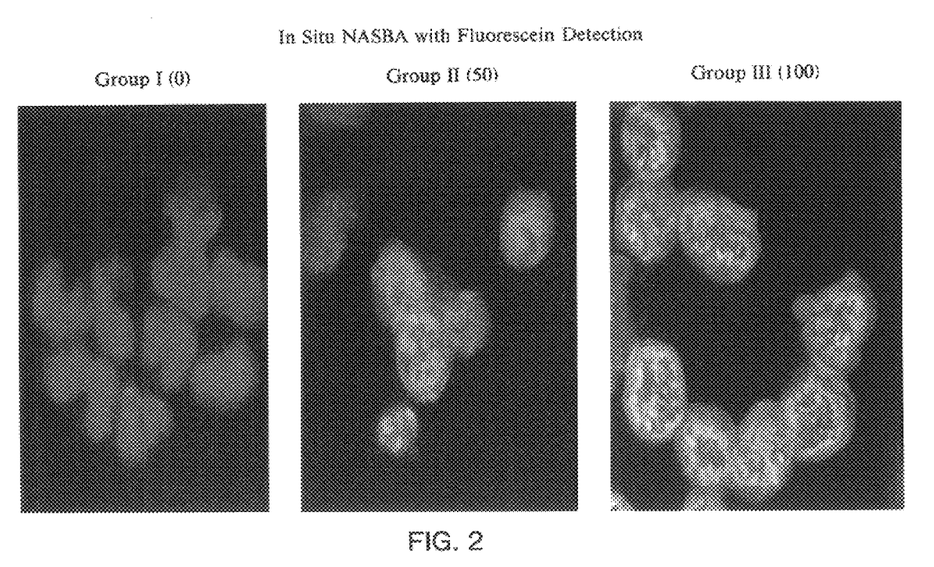
FIG. 2 shows fluorescein-conjugated anti-digoxigenin detection of H9 cells in situ in mixed cell populations of 0% infected cells, 50% infected cells and 100% infected cells, as described in Example 4.

For the remaining half of cells treated according to the in situ procedures in Example 1, including the use of FITC-labeled anti-dig antibodies, FIG. 2 shows that leakage from HIV-infected cells in Group II (50% infected) and Group III (100% infected) was prevented in the presence of molecular tape. This is shown in FIG. 2 (particularly in the Group III H9IIIB cells) by the localization of the fluorescein-labeled NASBA signals only in the cytoplasmic portion of the infected cells (as identified by the darker regions surrounding the lighter internal nuclear regions), which signals are absent from the medium surrounding the cells.

From these types of experiments, the ideal conditions for in situ isothermal amplification using molecular tape in accordance with the invention can be ascertained. Further, the skilled artisan would understand to modify the above procedures as necessary to practice the present invention using alternative amplification systems, such as thermal cycling-based systems.

EXAMPLE 5

Lymph node sections from a monkey infected with SIV and a monkey uninfected with SIV (both fixed with formalin) were dehydrated in xylene (2 times for 5 minutes each) and ethanol (two times for 5 minutes each) and rehydrated in ethanol (95%, 90%, 70%, and 50%, 2 minutes each). The sections were then subjected to Dispase II (0.6 U and 1.2 U, respectively) and a pronase mixture digestion for 30 minutes at 37° C. Digestion was followed by heat inactivation for 10 minutes at 90° C. The sections were then washed twice in PBS and twice in water, and dehydrated with ethanol (50%, 70%, 95%, and 100%, for 2 minutes each) and air dried.

Isothermal amplification was then performed as described above using primers from the GAG gene of SIV, as follows:

P1-AATTCTAATACGACTCACTATAGGGCACCAG-ATGACGCAGACAGTATTA (SEQ ID NO:3)
P2-CTCCGTCTTGTCAGGGAAGAAGCA.

Figure 3:
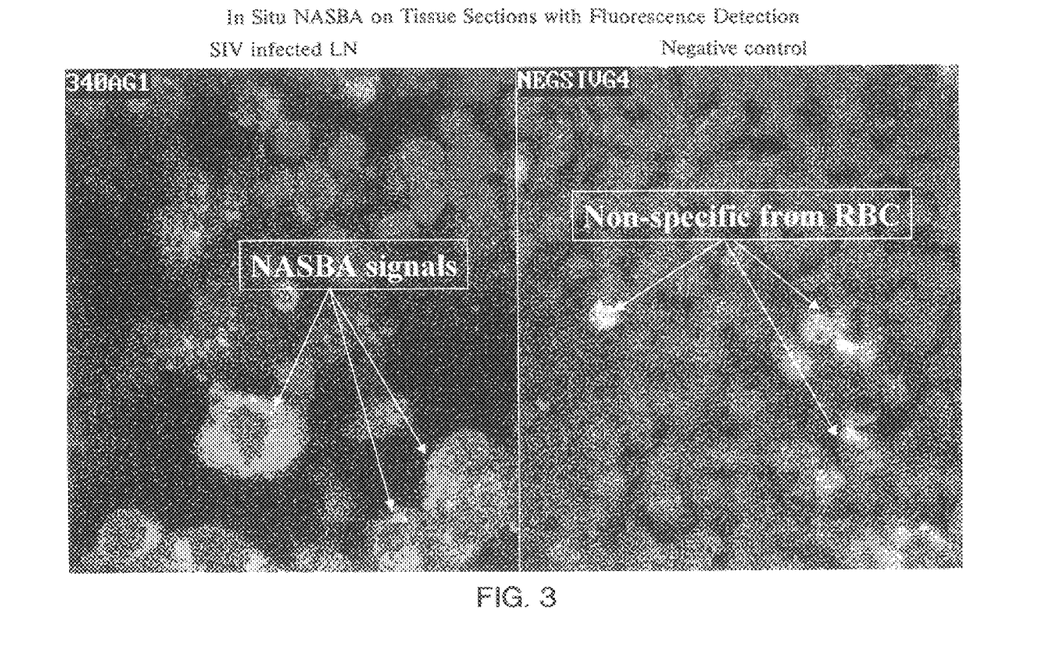
FIG. 3 shows fluorescein detection in situ of lymph node sections from a monkey infected with SIV, as described in Example 5.

FITC-labeled molecular tape was used as the detection probe, as well as for preventing leakage in accordance with the invention. The molecular tape contained the sequence: TTAGCTCCATTAGTGCCMCAGGCT-CAGCTCCGTCTTGTCAGGG (SEQ ID NO: 5), and was FITC-labeled at both the 5' and 3' ends of the molecule. FIG. 3 shows in the left-hand panel ("SIV infected LN") the localization of the NASBA signal to the cytoplasmic region of the cell, and the absence of fluorescein label in (and thus the prevention of leakage from the infected cells into) the surrounding medium.

In summary, the methods of the invention offer several significant advantages over other in situ amplification methods known in the art.

First, the molecular tape of the present invention permits the retention of small amplification products, thus allowing the amplification and detection of targets of any size.

Second, a preferred embodiment of isothermal transcription-based amplification allows specific amplification of RNA in a DNA background.

Third, the preferred embodiment of isothermal transcription-based amplification preserves cell morphology, thus providing information beyond what may be obtained using thermal cycling methods.

While the invention has been described in detail with reference to certain preferred embodiments thereof, it will be understood that modifications and variations are within the spirit and scope of that which is described and claimed.

What is claimed is:

1. A method for preventing an amplified target nucleic acid molecule from leaking from a cell, comprising the step of exposing the cell to molecular tape, which is a nucleic acid or a nucleic acid analog and does not function as a primer, wherein the molecular tape enters the cell and hybridizes with the amplified molecule to form a complex, and leakage is thereby prevented.

2. The method of claim 1, wherein the target nucleic acid molecule is amplified by isothermal amplification.

3. The method of claim 1, wherein the target nucleic acid molecule is amplified by thermal cycling amplification.

4. The method of claim 1, wherein the molecular tape further binds to one or more intracellular constituents.

5. The method of claim 1, wherein the target nucleic acid molecule is RNA.

6. The method of claim 1, wherein the target nucleic acid molecule is DNA.

7. The method of claim 1, wherein the target nucleic acid molecule is within a tissue section.

8. The method of claim 1, wherein the cell is one of a plurality of suspended cells.

9. The method of claim 1, further comprising the step of detecting the complex.

10. The method of claim 9, wherein the detection step occurs in situ.

11. The method of claim 10, wherein the molecular tape comprises a detectable label.

12. The method of claim 2, wherein the isothermal amplification is isothermal transcription-based amplification.

13. The method of claim 12, wherein the isothermal transcription-based amplification is nucleic acid sequence-based amplification (NASBA).

14. The method of claim 3, wherein the thermal cycling amplification is polymerase chain reaction (PCR).

15. The method of claim 3, wherein the thermal cycling amplification is reverse transcriptase PCR (RT-PCR).

16. The method of claim 1, wherein the molecular tape is single stranded.

17. The method of claim 1, wherein the molecular tape is double stranded.

18. The method of claim 1, wherein the molecular tape has a length of at least about 20 nucleotides.

19. The method of claim 18, wherein the length of the molecular tape ranges from about 20 to about 60 nucleotides.

20. The method of claim 19, wherein the length of the molecular tape ranges from about 30 to about 50 nucleotides.

21. The method of claim 1, further comprising the step of blocking the 3' end of the molecular tape.

22. The method of claim 1, wherein the cell is a fixed cell.

23. The method of claim 7, wherein the tissue section is a fixed tissue section.

24. The method of claim 1, wherein the molecular tape comprises DNA.

25. The method of claim 1, wherein the molecular tape comprises RNA.

26. The method of claim 1, wherein the molecular tape comprises a peptide-containing nucleic acid.

27. The method of claim 1, wherein a first sequence region of the molecular tape hybridizes with a complementary region of a first copy of the amplified target molecule, and a second sequence region of the molecular tape hybridizes with a complementary region of a second copy of the amplified target molecule.

28. The method of claim 1, wherein the molecular tape comprises a DNA analog.

29. The method of claim 1, wherein the molecular tape comprises an RNA analog.

* * * * *